United States Patent
Iwase et al.

(10) Patent No.: US 9,913,581 B2
(45) Date of Patent: Mar. 13, 2018

(54) PHOTOGRAPHY APPARATUS AND PHOTOGRAPHY METHOD

(71) Applicant: CANON KABUSHIKI KAISHA, Tokyo (JP)

(72) Inventors: Yoshihiko Iwase, Yokohama (JP); Makoto Sato, Tokyo (JP); Tomoyuki Makihira, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 12 days.

(21) Appl. No.: 14/909,054

(22) PCT Filed: Jul. 24, 2014

(86) PCT No.: PCT/JP2014/070147
§ 371 (c)(1),
(2) Date: Jan. 29, 2016

(87) PCT Pub. No.: WO2015/016291
PCT Pub. Date: Feb. 5, 2015

(65) Prior Publication Data
US 2016/0183785 A1    Jun. 30, 2016

(30) Foreign Application Priority Data

Jul. 31, 2013   (JP) ................................. 2013-159178

(51) Int. Cl.
| | |
|---|---|
| A61B 3/14 | (2006.01) |
| A61B 3/12 | (2006.01) |
| G01B 9/02 | (2006.01) |
| A61B 3/10 | (2006.01) |
| G06T 7/00 | (2017.01) |
| A61B 3/00 | (2006.01) |
| A61B 5/00 | (2006.01) |

(52) U.S. Cl.
CPC .......... *A61B 3/1225* (2013.01); *A61B 3/0025* (2013.01); *A61B 3/0058* (2013.01); *A61B 3/102* (2013.01); *A61B 3/14* (2013.01); *G01B 9/0203* (2013.01); *G01B 9/02091* (2013.01); *G06T 7/0016* (2013.01); *A61B 5/4842* (2013.01); *G01B 2290/70* (2013.01); *G06T 2207/10101* (2013.01); *G06T 2207/30041* (2013.01)

(58) Field of Classification Search
CPC ......... A61B 3/1225; A61B 3/14; A61B 3/102; A61B 3/0025; A61B 3/0058
USPC ................................................. 351/206, 246
See application file for complete search history.

(56) References Cited

FOREIGN PATENT DOCUMENTS

| JP | 2007-185244 A | 7/2007 |
| JP | 2012-213466 A | 11/2012 |
| WO | 2010/122118 A1 | 10/2010 |

*Primary Examiner* — Jack Dinh
(74) *Attorney, Agent, or Firm* — Canon U.S.A., Inc. IP Division

(57) ABSTRACT

To accurately position a past photography position and a photography position this time in follow up using polarization OCT images.

In follow up, multiple polarization-sensitive tomographic images are positioned based on multiple polarization planar images of an object, corresponding to multiple polarization-sensitive tomographic images obtained by photographing the object at another time.

18 Claims, 7 Drawing Sheets

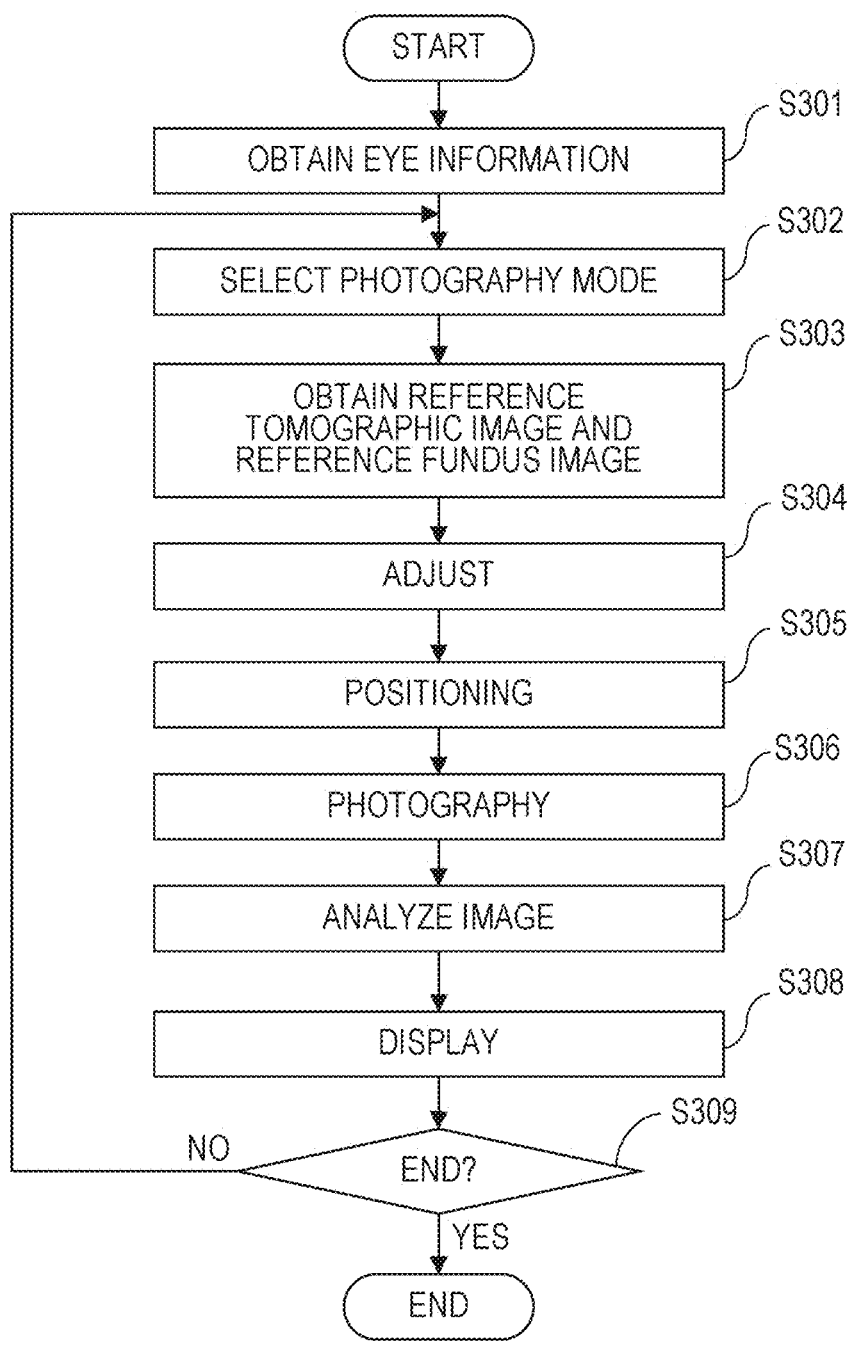

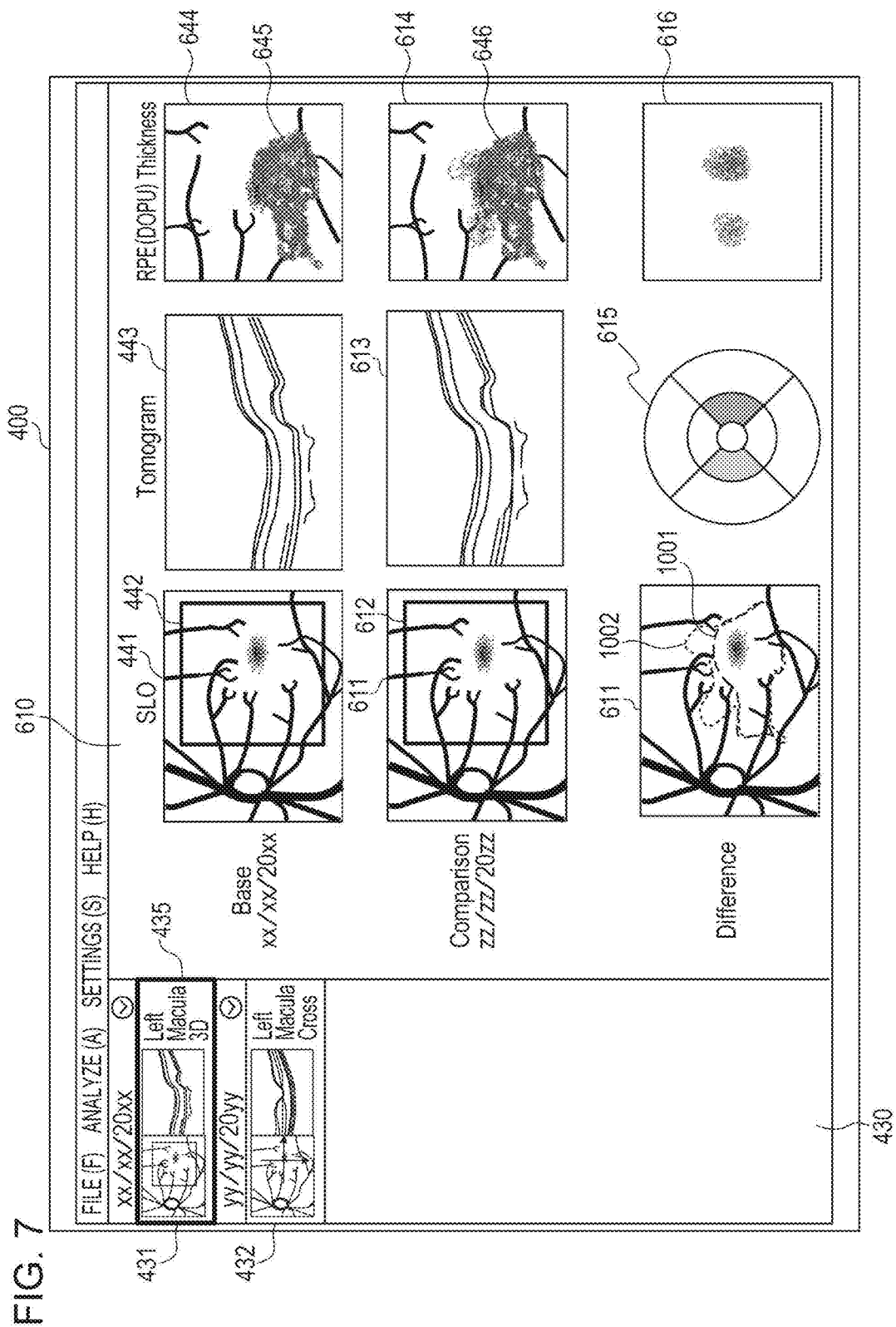

PHOTOGRAPHY APPARATUS AND PHOTOGRAPHY METHOD

TECHNICAL FIELD

The present invention relates to a photography apparatus and photography method to photograph an object.

BACKGROUND ART

Optical coherence tomography (OCT) using multi-wavelength light-wave interference can obtain tomographic images of specimens (particularly the fundus) at high resolution.

In recent years, ophthalmologic OCT apparatuses have come to acquire polarization sensitive OCT images using polarization parameters (retardation and orientation) which are a type of optical properties of fundus tissue, in addition to normal OCT images where the shape of the fundus tissue is imaged.

A polarization sensitive OCT image can be configured and fundus tissue can be distinguished and segmented using polarization parameters in polarization sensitive OCT. PTL 1 discloses that in polarization sensitive OCT, light which has been modulated into circularly-polarized light is used as measurement light to observe a specimen, and interference light is split as two orthogonal linearly-polarized lights and detected, thereby generating a polarization sensitive OCT image.

PTL 2 discloses storing scanning position information indicating a scanning position of signal light when a tomographic image was formed in the past, to avoid tests with an ophthalmologic OCT apparatus taking a long time, and to alleviate burdensome tasks. PTL 2 discloses that upon eye identification information being input, operation position information correlated with the input identification information is searched, and signal light is scanned based on the searched scanning position information.

CITATION LIST

Patent Literature

PTL 1 International Publication No. WO2010/122118A1
PTL 2 Japanese Patent Laid-Open No. 2007-185244

SUMMARY OF INVENTION

Solution to Problem

A photography apparatus according to the present invention includes: a selecting unit configured to select one of a plurality of photography modes, including a follow up photography mode; a tomographic image acquiring unit configured to acquire a plurality of polarization-sensitive tomographic images obtained by photographing an object at different times; and a positioning unit configured to, in a case where the follow up photography mode has been selected, position the plurality of polarization-sensitive tomographic images based on a plurality of polarization planar images of the object corresponding to the plurality of polarization-sensitive tomographic images.

A photography method according to the present invention includes: a step to select one of a plurality of photography modes, including a follow up photography mode; a step to acquire a plurality of polarization-sensitive tomographic images obtained by photographing an object at different times; and a step to, in a case where the follow up photography mode has been selected, position the plurality of polarization-sensitive tomographic images based on a plurality of polarization planar images of the object corresponding to the plurality of polarization-sensitive tomographic images.

Further features of the present invention will become apparent from the following description of exemplary embodiments with reference to the attached drawings.

BRIEF DESCRIPTION OF DRAWINGS

FIG. 3 is a flowchart illustrating processing according to the first embodiment.

FIG. 7 is a display example of a display screen on a display unit of the image processing apparatus according to a fourth embodiment.

DESCRIPTION OF EMBODIMENTS

It has been found desirable to accurately match past photography positions with a current photography position in follow-up using polarization sensitive OCT images. According to an embodiment, in a case where a follow-up photography mode is selected, multiple polarization-sensitive tomographic images are positioned, based on multiple polarization planar images of an object which correspond to multiple polarization-sensitive tomographic images of the object, shot at different times. Accordingly, past photography positions can be accurately matched with a current photography position in follow-up using polarization sensitive OCT images. A photography apparatus according to the present invention can be applied to objects such as eyes, skin, internal organs, and so forth. Examples of photography apparatuses according to the present invention include ophthalmologic apparatuses, endoscopes, and so forth. An ophthalmologic apparatus according to an embodiment will be described in detail with reference to the drawings, as an example of the present invention.

Overall Configuration of Apparatus

Figure 1:
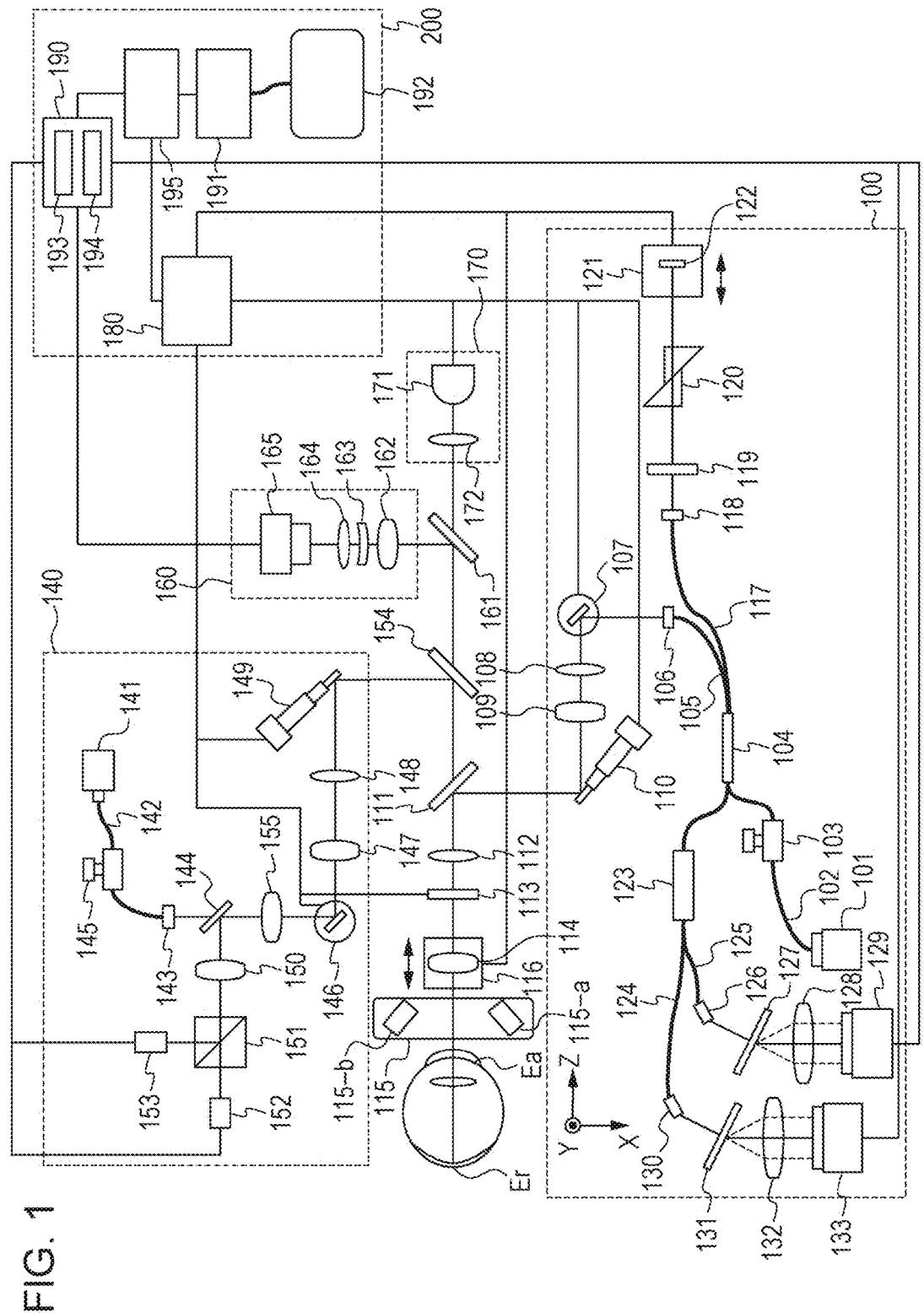
FIG. 1 is a schematic diagram of the overall configuration of an image processing apparatus according to a first embodiment.

FIG. 1 is a schematic diagram illustrating the overall configuration of an image processing apparatus according to the present embodiment. At least part of a later-described signal processing unit 190 can be deemed to be an "image processing apparatus", in which case the overall "ophthalmologic apparatus" can be deemed to be an "ophthalmologic system", and the overall "photography apparatus" can be deemed to be a "photography system".

The present apparatus is configured including a polarization sensitive OCT (PS-OCT) apparatus 100, a polarization sensitive scanning laser ophthalmoscope (PS-SLO) 140, an anterior ocular segment imaging unit 160, an interior fixation lamp 170, and a control unit 200.

In a state where the interior fixation lamp 170 is turned on and the eye gazing the interior fixation lamp 170, alignment of the apparatus is performed using an anterior ocular segment image of the eye as observed by the anterior ocular segment imaging unit 160. After alignment is completed, fundus imaging is performed by the PS-OCT apparatus 100 and PS-SLO 140.

Configuration of PS-OCT Apparatus 100

The configuration of the PS-OCT apparatus 100 will now be described. First, the light source 101 emits light having a center wavelength of 850 nm and a bandwidth of 50 nm, for example. Although an SLD is described as being used for the light source 101, any light source capable of emitting low-coherence light may be used, such as an amplified spontaneous emission (ASE) light source, for example.

The light emitted from the light source 101 is guided to a fiber coupler 104 having polarization-maintaining functions, via a PM fiber 102 and polarization controller 103, and splits into measurement light (hereinafter also referred to as "OCT measurement light"), and reference light (also referred to as "reference light corresponding to the OCT measurement light"). Also, the polarization controller 103 adjusts the state of polarization of the light emitted from the light source 101 so as to be adjusted to linearly-polarized light. The branching ratio at the fiber coupler 104 is reference light 90 to measurement light 10.

The branched measurement light, is emitted as parallel light from a collimator 106 via a PM fiber 105. The emitted measurement light passes through an X-scanner 107 made up of a galvano mirror which scans the measurement light in the horizontal direction at a fundus Er, lenses 108 and 109, and a Y-scanner 110 made up of a galvano mirror which scans the measurement light in the vertical direction at the fundus Er, and reaches a dichroic mirror 111. The X-scanner 107 and Y-scanner 110 are controlled by a driving control unit 180, and can scan measurement light over a predetermined range of the fundus Er (also referred to as acquisition range of tomographic image, acquisition position of tomographic image, and light-casting position for measurement light). The dichroic mirror 111 has properties where light of 800 nm to 900 nm is reflected, and other light is transmitted.

The measurement light reflected by the dichroic mirror 111 passes via a lens 112 and through a λ/4 polarization plate 113 (example of polarization adjusting member) inclined at a 45 degrees angle. Thus the phase is shifted by 90 degrees, so the polarization of the light is controlled to be circularly-polarized light. The inclination of the λ/4 polarization plate 113 is preferably polarization splitting face of a polarization beam splitter included in the fiber coupler 123, from the optical axis, for example (example of array state).

The λ/4 polarization plate 113 is preferably configured to be extractably inserted to the optical path. For example, a mechanical configuration where the λ/4 polarization plate 113 is rotated on an axis parallel to the optical axis can be conceived. This can realize a small apparatus in which the SLO optical system and PS-SLO optical system can be easily switched between. Also, this can realize a small apparatus in which the OCT optical system and PS-OCT optical system can be easily switched between.

Now, the light input to the eye has the polarization thereof controlled to be circularly-polarized light by the λ/4 polarization plate 113 being installed at a 45 degree angle. However, there are cases where the light is not circularly-polarized light at the fundus Er, due to properties of the eye. Accordingly, the λ/4 polarization plate 113 is configured such that the inclination thereof can be fine-adjusted under control of the driving control unit 180.

The measurement light of which the polarization has been controlled to be circularly-polarized light is focused on a retina layer of the fundus Er by a focus lens 114 on a stage 116, via an anterior ocular segment Ea which is the object. The measurement light cast upon the fundus Er is reflected/scatter at each retina layer, and returns on the optical path to the fiber coupler 104.

The reference light which has branched at the fiber coupler 104 passes through a PM fiber 117 and is emitted from a collimator 118 as parallel light. The emitted reference light is subjected to polarization control by a λ/4 polarization plate 119 inclined at a 22.5 degrees angle from p-polarized light to s-polarized light, in the same way as the measurement light. The reference light passes through a dispersion compensation glass 120, is reflected at a mirror 122 on a coherence gate stage 121, and returns to the fiber coupler 104. The reference light passes through the λ/4 polarization plate 119 twice, whereby linearly-polarized light returns to the fiber coupler 104. The coherence gate stage 121 is controlled by the driving control unit 180 to deal with difference in the axial length of the eye of the object, and so forth.

The measurement light which has returned to the fiber coupler 104 and the reference light are multiplexed to form interference light, which is input to a fiber coupler 123 including a polarization beam splitter, and split into p-polarized light and s-polarized light which have different polarization directions, at a branching ratio of 50 to 50 in the present embodiment.

The p-polarized light passes through a PM fiber 124 and collimator 130, is dispersed at grating 131, and received at a lens 132 and line camera 133. In the same way, the s-polarized light passes through a PM fiber 125 and collimator 126, is dispersed at grating 127, and received at a lens 128 and line camera 129. Note that the grating 127 and 131, and line cameras 129 and 133 are positioned in accordance to each polarization direction. The light received at each of the line cameras 129 and 133 is output as electric signals in accordance to the intensity of light, and received at the signal processing unit 190 (example of tomographic image generating unit).

While the inclination of the λ/4 polarization plates 113 is described as being adjusted with reference to the polarization beam splitter, an arrangement may be made where the inclination is adjusted as to a line connecting the center of the optic disc and the center of a macula. Also, the same effects can be obtained by adjusting the polarization beam splitter and λ/4 polarization plates 113 and 119 with the vertical direction as the reference.

Configuration of PS-SLO 140

The configuration of the PS-SLO 140 will now be described. First, a light source 141 is a semiconductor layer which emits light having a center wavelength of 780 nm, for example, in the present embodiment. The measurement light emitted from the light source 141 (hereinafter also referred to as "SLO measurement light") passes through a PM fiber 142, the polarization thereof is controlled at a polarization controller 145 so as to become linearly-polarized light, and is output from a collimator 143 as Parallel light. The emitted measurement light passes through the perforation of a perforated mirror 144, passes through a lens 155, passes through an X-scanner 146 made up of a galvano mirror which scans the measurement light in the horizontal direction at a fundus Er, lenses 147 and 148, and a Y-scanner 149 made up of a galvano mirror which scans the measurement light in the vertical direction at the fundus Er, and reaches a dichroic mirror 154. The X-scanner 146 and Y-scanner 149 are controlled by the driving control unit 180, and can scan measurement light over a predetermined range of the fundus Er. The dichroic mirror 154 has properties where light of 760 nm to 800 nm is reflected, and other light is transmitted. The linearly-polarized light measurement light reflected at the dichroic mirror 154 passes over the same optical path as with the PS-OCT apparatus 100, and reaches the fundus Er.

The measurement light which has been cast on the fundus Er is reflected/scatter at the fundus Er, and returns on the above-described optical path to reach the perforated mirror 144. The light reflected at the perforated mirror 144 passes through a lens 150 and is input to a polarization beam splitter 151, and split into light which have different polarization directions (p-polarized light, and s-polarized light in the present embodiment), received at avalanche photodiodes (APD) 152 and 153 and converted into electric signals, which are received at the signal processing unit 190 (example of fundus image generating unit).

The position of the perforated mirror 144 is conjugate with the pupil position of the eye. Of the measurement light cast on the fundus Er and reflected/scattered, the light which has passed through around the pupil is reflected by the perforated mirror 144.

While PM fibers have been used for both the PS-OCT apparatus and PS-SLO in the present embodiment, the same configuration and effects can be obtained by controlling polarization using a polarization controller even if using single mode fiber (SMF).

Anterior Ocular Segment Imaging Unit 160

The anterior ocular segment imaging unit 160 will now be described. The anterior ocular segment imaging unit 160 illuminates the anterior ocular segment Ea using an illumination light source 115 including LED 115-a and 115-b which emit illumination light having a wavelength of 1000 nm. The light, reflected at the anterior ocular segment Ea passes through the lens 114, polarization plate 113, lens 112, dichroic mirrors 111 and 154, and reaches a dichroic mirror 161. The dichroic mirror 161 has properties where light of 980 nm to 1100 nm is reflected, and other light is transmitted. The light reflected at the dichroic mirror 161 passes through lenses 162, 163, and 164, and is received at an anterior ocular segment camera 165. The light received at the anterior ocular segment camera 165 is converted into electric signals, and received at the signal processing unit 190.

Interior Fixation Lamp 170

The interior fixation lamp 170 will now be described. The interior fixation lamp 170 is configured including an interior fixation lamp display unit 171 and a lens 172. The interior fixation lamp display unit 171 includes multiple light-emitting diodes (LEDs) arrayed in a matrix. The lighting position of the LEDs is changed in accordance with the region to be imaged, under control of the driving control unit 180. Light from the interior fixation lamp display unit 171 is guided to the eye via the lens 172. The light emitted from the interior fixation lamp display unit 171 has a wavelength of 520 nm, and a desired pattern is displayed by the driving control unit 180.

Control Unit 200

The control unit 200 which controls the overall apparatus will now be described. The control unit 200 includes the driving control unit 180, the signal processing unit 190, a display control unit 191, a display unit 192, and a positioning unit 195. The driving control unit 180 controls each part as described above. The signal processing unit 190 includes an image generating unit 193 and an image analyzing unit 194. The signal processing unit 190 generates images, analyzes the generated images, and generates visualization information of the analysis results, based on signals output from each of the line cameras 129 and 133, APDs 152 and 153, and anterior ocular segment camera 165. Details of generating and analyzing images will be described later.

The display control unit 191 displays fundus images and fundus tomographic images, and so forth, generated at a fundus image acquiring unit and tomographic image acquiring unit (both omitted from illustration), on a display screen of the display unit 192. The display unit 192 here is a liquid crystal display or the like. The image data generated at the signal processing unit 190 may be transmitted to the display control unit 191 by cable, or wirelessly. In this case, the display control unit 191 can be deemed to be an image processing apparatus. An arrangement may be made for the photography system where a fundus image acquisition unit includes an SLO optical system, and a tomographic image acquisition unit includes an OCT optical system. In the present Specification, if the object includes other than an eye, the term "fundus image (fundus luminesce image)" can be rephrased as "planar image "planar luminesce image)", and the term "fundus image acquisition unit" can be rephrased as "planar image acquisition unit".

The display unit 192 displays various types of information in various display formats under control of the display control unit 191, as described later. The image data from the display control unit 191 may be transmitted to the display unit 192 by cable, or wirelessly. While the display unit 192 and other units are illustrated as being included in the control unit 200, but the present invention is not restricted to this, and may be provided separately from the control unit 200. Also, the display control unit 191 and display unit 192 may be integrally formed as a device which can be carried by the user (tablet). In this case, the display unit preferably has a touch panel function, so that the display position can be moved, enlarged, or reduced, and the displayed image can be changed, or the like, by performing operations on the touch panel.

Image Processing

Next, image generating at the image generating unit 193 will be described.

Generating Tomographic Image, and Generating Fundus Image

The image generating unit 193 performs reconstruction processing commonly used in spectral domain (SD) OCT on interference signals output from the line cameras 129 and 133, thereby generating two tomographic images based on each polarization component. The two tomographic images are a tomographic luminance image corresponding to first polarization light, and a tomographic luminance image corresponding to second polarization light.

First, the image generating unit 193 removes fixed pattern noise from the interference signals. Removal of the fixed pattern noise is performed by extracting the fixed pattern noise by averaging multiple A-scan signals that have been detected and subtracting the fixed pattern noise from the input interference signals.

Next, the image generating unit 193 converts the interference signals from wavelength to wavenumber, and performs Fourier transform, thereby generating tomography signals (also called polarization-sensitive tomography signals).

Performing the above-described processing on the interference signals of the two polarization components generates two tomographic images.

The image generating unit 193 arrays the signals output from the APDs 152 and 153 synchronously with the driving of the X-scanner 146 and Y-scanner 149, thereby generating two fundus images based on the respective polarization components. The two fundus images are a fundus image corresponding to the first polarization light, and a fundus image corresponding to the second polarization light.

Generating Luminance Image

The image generating unit 193 generates a luminance image from the two aforementioned tomography signals. The luminance image is basically the same as a tomographic images in conventional OCT. A pixel value r thereof is calculated from tomography signals $A_H$ and $A_V$ obtained from the line sensors 129 and 133, as calculated by Expression (1).

[Math. 1]

$$r = \sqrt{A^2_H + A^2_V}$$  Expression (1)

A fundus luminance image is also generated from the two fundus images in the same way.

Figure 2E:
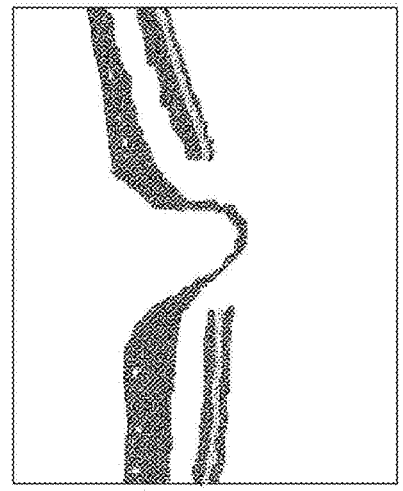
FIGS. 2A through 2E are examples of images generated at a signal processing unit according to the first embodiment.
Figure 2B:
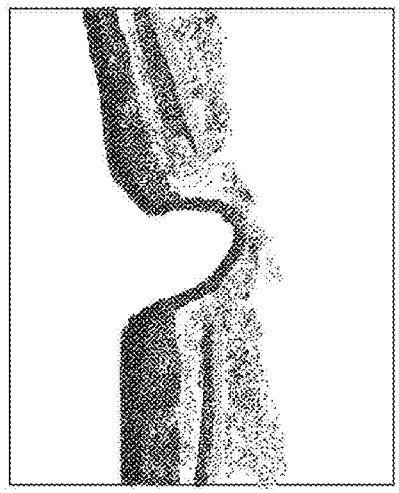
Figure 2D:
Figure 2A:
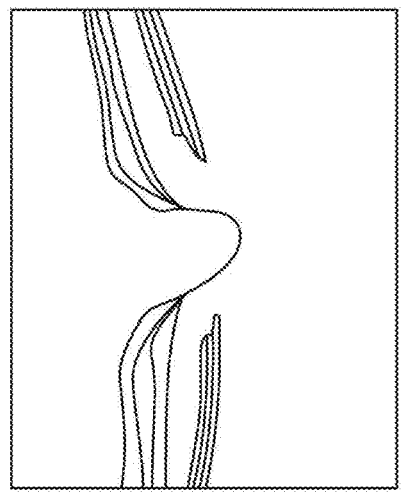
Figure 2C:
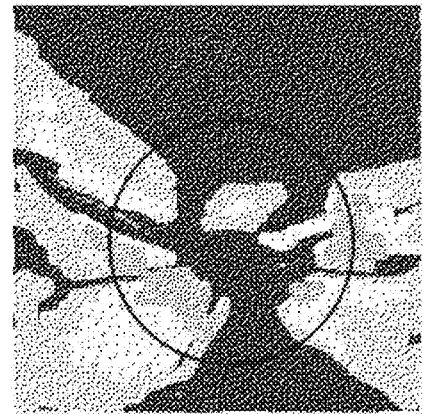

FIG. 2A illustrates an example of a luminance image of an optic disc.

Generating Retardation Image

The image generating unit 193 generates retardation images from tomographic images of mutually orthogonal polarization components. A value δ of each pixel of the retardation image is a value representing the difference in phase between the vertical polarization component and horizontal polarization component, at the position of each pixel in the tomographic image, calculated from the tomography signals $A_H$ and $A_V$ by the following Expression (2).

[Math. 2]

$$\delta = \arctan\left[\frac{A_V}{A_H}\right]$$  Expression (2)

FIG. 2B illustrates art example of a retardation image of the optic disc generated in this way (also referred to as tomographic image indicating phase difference of polarized light), and can be obtained by performing calculation according to Expression (z) on each B-scan image. FIG. 2B is a color display to values representing the above phase difference as a tomographic image. Dark portions indicate a small value for the phase difference, and light portions indicate a great value for the phase difference. Accordingly, layers with birefringence can be comprehended by generating a retardation image.

Generating Retardation Map

The image generating unit 193 generates a retardation map from the retardation image obtained with regard to multiple B-scan images. The image generating unit. 193 first detects the retinal pigment epithelium (RPE layer) in each B-scan image. The RPE layer has a nature of cancelling polarized light, so retardation distribution is inspected in each A-scan image in the depth direction, from the inner limiting membrane (ILM) over a range not including the RPE. The maximum value thereof is the representative value of retardation in the A-scan.

The image generating unit 193 performs the above processing on all retardation images, thereby generating a retardation map.

FIG. 2O illustrates an example of a retardation map of the optic disc. Dark portions indicate a small value for the phase difference, and light portions indicate a great value for the phase difference. The retinal nerve fiber layer (RNFL) is a layer having birefringence at the optic disc. The retardation map is an image illustrating the difference in phase due to the birefringence of the RNFL and the thickness of the RNFL. Accordingly, the phase difference is great when the RNFL is thick, and the phase difference is small when the RNFL is thin. Thus, the retardation map enables the thickness of the RNFL to be comprehended for the overall fundus, which can be used in diagnosis of glaucoma.

Generating Birefringence Map

The image generating unit 193 linearly approximates the value of retardation δ in the range of the ILM to the RNFL, in each A-scan image of the retardation images generated earlier, and determines the inclination thereof to be the birefringence at the position of the A-scan image on the retina. This processing is performed on all retardation images that have been acquired, thereby generating a map representing birefringence.

FIG. 2D illustrates an example of a birefringence map of the optic disc. The birefringence map directly maps birefringence values, so even if the thickness of the RNFL does not change, change in the fiber structure thereof can be visualized as change in birefringence.

Generating a DOPU Image

The image generating unit 193 calculates a Stokes vector S for each pixel, from the obtained tomography signals $A_H$ and $A_V$, and the phase difference $\Delta\Phi$ therebetween, by the following Expression (3),

[Math. 3]

$$S = \begin{pmatrix} I \\ Q \\ U \\ V \end{pmatrix} = \begin{pmatrix} A_H^2 + A_V^2 \\ A_H^2 - A_V^2 \\ 2A_H A_V \cos\Delta\phi \\ 2A_H A_V \sin\Delta\phi \end{pmatrix}$$  Expression (3)

where $\Delta\Phi$ has been calculated from $\Delta\Phi = \Phi_V - \Phi_H$, from the phases $\Phi_H$ and $\Phi_V$ of each signal obtained at the time of calculating the two tomographic images.

The image generating unit 193 sets a window for each B-scan image of a size around 70 μm in the main scanning direction of the measurement light and 18 μm in the depth direction, averages each element of the Stokes vector calculated for each pixel by Expression (3) within each window, and calculates the degree of polarization uniformity (DOPU) in each window by Expression (4),

[Math. 4]

$$\text{DOPU} = \sqrt{Q^2_m + U^2_m + V^2_m}$$  Expression (4)

where $Q_m$, $U_m$, and $V_m$ are each values of the averaged Stokes vector elements Q, U, and V in each window.

This processing is performed on all windows within the B-scan image, thereby generating a DOPU image of the optic disc illustrated in FIG. 2E (a tomographic image indicating the uniformity of polarized light).

DOPU is a numerical value representing uniformity of polarized light. At locations where polarization is maintained, the value is near 1, and the value is smaller than 1 at locations where polarization is cancelled and not maintained. The RPE has a nature of cancelling the polarization state, so the portions in the DOPU image corresponding to the RPE exhibit a smaller value as compared to other regions. The light portion 210 in FIG. 2E represents the RPE, and the dark portion 220 represents the retinal layer region where polarization is maintained. The DOPU image visualizes layers where polarization is cancelled, such as the RPE and so forth, so even in a case where the RPE has been deformed by a disease or the like, the RPE can be visualized in a more sure manner than change in luminance.

Note that in the present Specification, the above-described tomographic images corresponding to the first and second polarized light, retardation images, DOPU images, and so forth, may also be referred to as "tomographic images indicating polarization state" or "polarization-sensitive tomographic images". Also in the present Specification, the above-described retardation map and birefringence map and so forth may also be referred to as "fundus image indicating polarization state" or "polarization fundus image". In cases of including other objects than the eye, the polarization fundus image may be referred to as "polarization planar image".

Processing Operations

Figure 4:
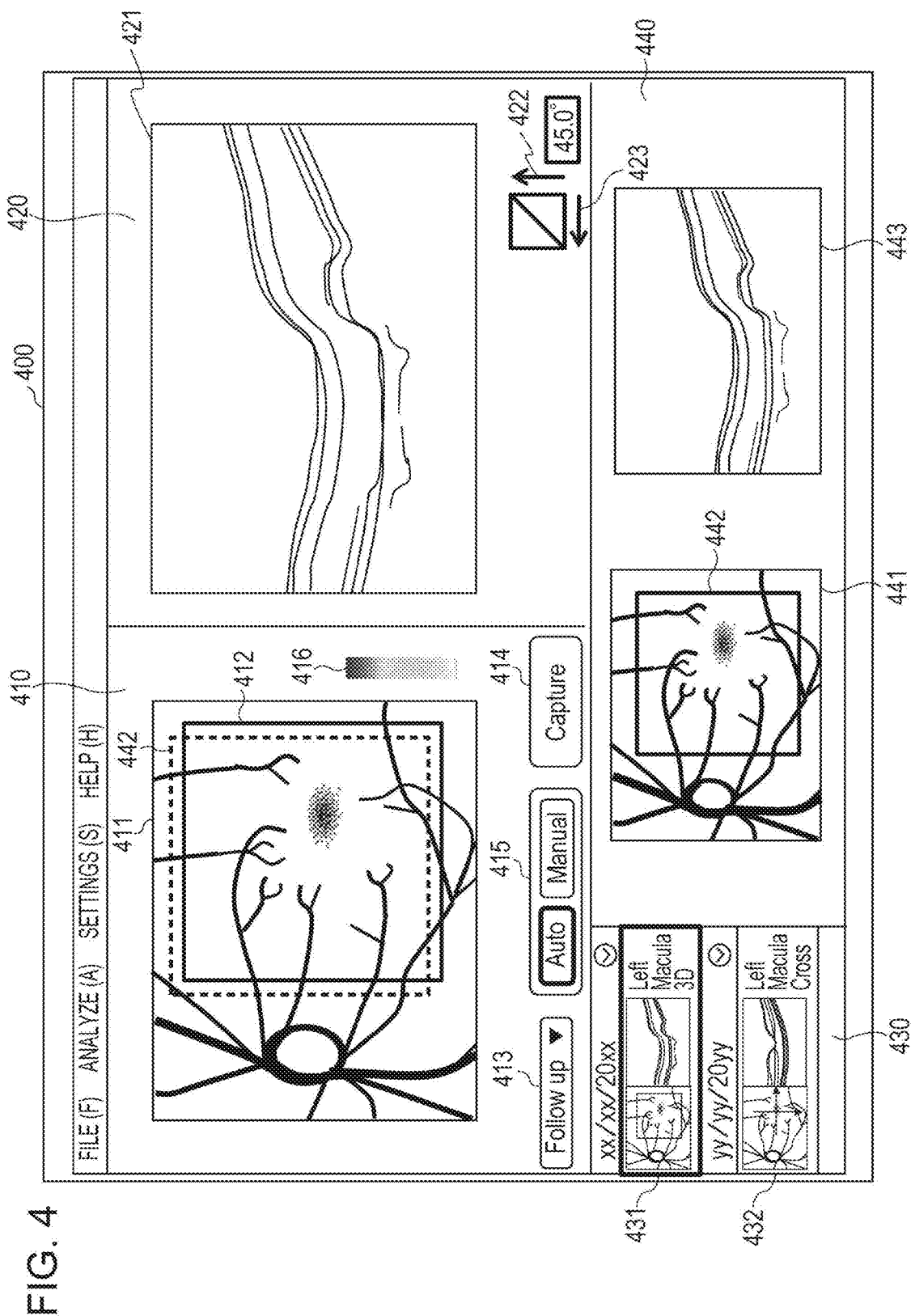
FIG. 4 is a display example of a display screen on a display unit of the image processing apparatus according to the first embodiment.

Next, processing operations by the image processing apparatus according to the present embodiment will be described with reference to FIGS. 3 and 4. This processing is to perform evaluation in follow up by comparing with tomographic images of the eye and fundus images taken at another time. FIG. 3 is a flowchart illustrating the processing operations performed by the image processing apparatus according to the present embodiment, and FIG. 4 illustrates an example of a display screen (window) 400 displayed on the display unit 192 according to the present embodiment when performing photography. In FIG. 4, the display screen 400 is a tomographic image photography screen, including display regions 410, 420, 430, and 440. Reference numeral 421 denotes a tomographic image, 411 denotes a fundus image, 413 a combo box for selecting photography mode, 414 a capture instruction button for instructing execution of photography, 415 a positioning selection button to select whether to perform positioning manually or automatically, and 412 a mark indicating a photography region which is displayed superimposed on the fundus image 411.

Step S301: Obtaining Eye Information

In step S301, an eye information acquiring unit, omitted from illustration, externally acquires an object identification No. which is an example of identification information of the eye, used to identify the eye. Information relating to the eye that is held in a storage unit, omitted from illustration, is obtained based on the object identification No. Examples of information relating to the eye include personal information such as name, gender, age, medical history, and so forth, image data such as fundus images and tomographic images, and analysis data such as image analysis.

Step S302: Selecting Photography Mode

In step S302, a photography mode is selected. Description will be made assuming that selection of the photography mode is made from the combo box 413 for selecting the photography mode. The combo box 413 functions such that input can be directly made to a text box, and also pressing a button to the right end of the text box displays a list of selectable items, from which one can be selected. Normal photography mode, and follow up photography mode can be selected from the combo box 413. The combo box 413 may be configured to enable selection of one photography mode from multiple photography modes including these and other photography modes. Description will be made in the present embodiment regarding a case of performing photography in the follow up photography mode.

Step S303: Obtaining Reference Image for Positioning

Upon the follow up photography mode being selected in step S302, thumbnails 431 and 432 of image data for the same object that has been shot in the past, is displayed in the region 430. This past image data has been searched from the storage unit based on the input object identification No. The operator selects one of the displayed thumbnails as a reference image, upon which the fundus image 441 and tomographic image 443 are displayed in the region 440. The present embodiment illustrates an example of a case where the thumbnail 431 has been selected. The thumbnail 431 is data where 3D photography has been performed of the macula. Selecting past photography data in the follow up mode brings up the fundus image 441 and tomographic image 443 in the region 440. The fundus image 411 has superimposed thereupon a photography region frame 442 indicating a photography region of the past photography.

Step S304: Adjustment

In step S304, alignment of the apparatus and the eye is performed with the eye set to the apparatus. Description will be made regarding alignment unique to the present specification, and general adjustments such as XYZ alignment of working distance and so forth, focusing, coherence gate adjustment, and so forth will be omitted from description. Adjustment of the λ/4 polarization plate 113 will be described here.

FIG. 4 illustrates the window 400 displayed on the display unit 192 when performing adjustment. In FIG. 4, instruction portions 422 and 423 are displays to adjust the angle of the λ/4 polarization plate 113. The angle of the λ/4 polarization plate 113 is adjusted by the operating giving instructions using the instruction device, under control of the driving control unit 180. The instruction portion 422 is a display for instructing adjustment in the counter-clockwise direction, and the instruction portion 423 is a display for instructing adjustment in the clockwise direction. The numerical value displayed to the side of the instruction portions 422 and 423 indicates the current angle of the λ/4 polarization plate 113. A tomographic image 421 generated from p-polarized light and s-polarized light is displayed in the display region 420.

The order of adjustment preferably is alignment adjustment using anterior ocular segment images or corneal bright points, focus adjustment using polarization fundus images, coherence gate adjustment using polarization-sensitive tomographic luminance images, and adjustment of the λ/4 polarization plate 113. While the acquisition position of the tomographic luminance image indicating polarization state is preferably decided before the coherence gate adjustment using polarization-sensitive tomographic images, this may be decided at an initial settings screen so as to acquire the center region of the fundus image indicating polarization state. Accordingly, tomographic luminance images indicating polarization state which can handle finer and narrower ranges than fundus images indicating polarization state can be accurately acquired by simple adjustment. At this time, the λ/4 polarization plate 113 may be automatically adjusted in accordance with completion of the coherence gate adjustment, or the λ/4 polarization plate 113 may be automatically adjusted in accordance with input of a signal to acquire an image indicating polarization state. Of course, a configuration may be made where the λ/4 polarization plate 113 is adjusted beforehand at the initial settings screen upon startup of the ophthalmologic apparatus, and not adjusted each time photography is performed. Further, parameters adjusted when shooting the tomographic image selected as the reference tomographic image may be used.

These adjustments may all be performed automatically in the above-described order, or sliders may be displayed on the display unit corresponding to each adjustment, and the cursor used to perform drag operations for adjustment.

Step S305: Positioning

In step S305, positioning is performed to shoot the same position as the reference image selected in step S303, for follow up. Description will be made in the present embodiment regarding a case where Auto has been selected by the positioning selection button 415. The image overlaying unit 195 performs positioning using a polarization component map (e.g., retardation map) created when shooting the reference image selected in step S303, and a polarization component map created by the eye while performing alignment. Description will be made with reference to FIGS. 5A through 5D regarding a case of using a polarization component map for positioning.

Figure 5A:
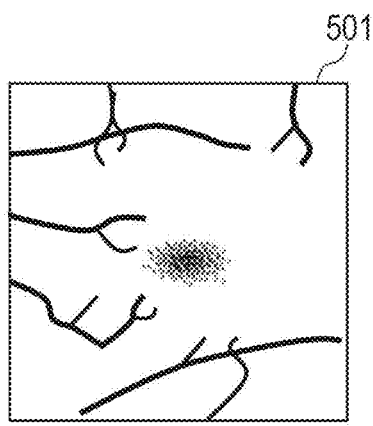
FIGS. 5A through 5D are diagram for describing polarization component images according to the first embodiment.
Figure 5B:
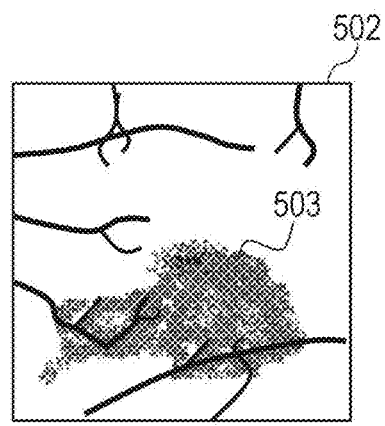
Figure 5C:
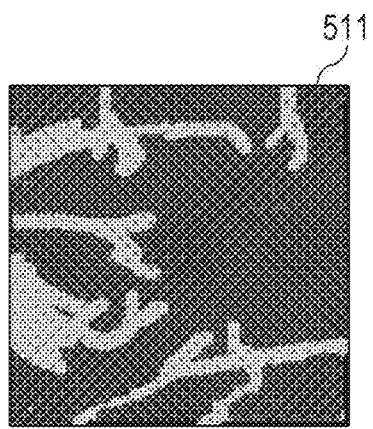
Figure 5D:
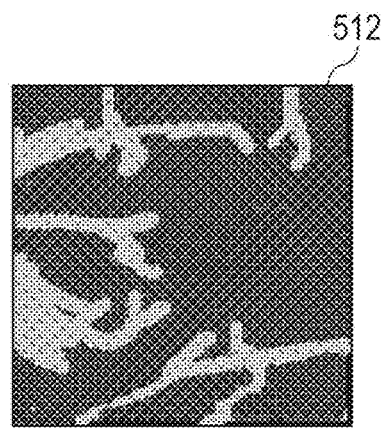

For example, around the RPE can be deformed due to change in form of the retina or hemorrhaging, caused by age-related macular degeneration (AND) where the macula degenerates due to age, branch retinal vein occlusion (BRVO) where the veins in the retina become clogged and blow stops flowing, and so forth. In such cases image features of the integrated image created from SLO images and tomographic images change. This is illustrated in FIGS. 5A through 5D. FIG. 5A illustrates an integrated image 501 created from tomographic images in a case where no pathological abnormality is present. FIG. 5B illustrates a case of an integrated image 502 created from tomographic images where AND 503 is present. The term "integrated image" means a luminance image which has been created by integrating the A scans in tomographic images in the depth direction. Image features are not the same between cases where a disease is present and where there is not, as can be seen from FIGS. 5A and 5B. On the other hand, FIG. 5C is a retardation map 511 created from tomographic images in a case where no pathological abnormality is present, and FIG. 5D is a retardation map 512 created from tomographic images in a case where AMD 503 is present. As can be seen from FIGS. 5C and 5D, there is little difference between the polarization component maps. This is because luminance images such as integrated images and SLO images visualize the change due the disease around the RPE, but retardation maps using polarization components visualize layer having birefringence. In the present embodiment, the RNFL is visualized, so there is little influence of the disease occurring around the RPE, and a map where polarization components are visualized is used for automatic positioning between a past fundus image and the eye in alignment. In contrast, cases of using integrated images of tomographic luminance images can result in great change in image feature amounts if the integrated image changes due to disease or disorder such as hemorrhaging or AND or the like. Accordingly, positioning using integrated images of polarization-sensitive tomographic images is preferably performed, to avoid deterioration in positioning accuracy as to the integrated image from the previous time.

An example of a positioning method for follow up is to define beforehand an evaluation function representing the similarity of two images (a polarization fundus image acquired in the past and a polarization fundus image newly acquired), and to deform the images (e.g., parallel movement, rotation, enlarging, reduction) so that the value of the evaluation function is the best. An example of an evaluation function is a method to evaluate by luminance values (e.g., a method to evaluate using correlation coefficients). Another example of image deformation is processing involving translation and rotation using affine transform. Alternatively, positioning may be performed using phase-only correlation (POC) where phase properties are correlated, instead of using luminance values of the images.

In a case of a disease such as glaucoma which changes the RNFL, a DOPU map generated from DOPU images may be used for the polarization component map instead of a retardation map.

Setting of the photography range is performed under control of the driving control unit 180, based on the positioning results by the image overlaying unit 195. Thus, the driving control unit 180 sets the photography range for controlling the driving angle of the scanner, so as to photograph the position which the image overlaying unit 195 has calculated.

Step S306: Photography

A fundus image 411 imaged by the PS-SLO 140 and generated at the signal processing unit 190 (also referred to as luminance fundus image or two-dimensional fundus image) is displayed in the display region 410 (also referred to as first display region) in FIG. 4. A solid line frame 412 indicating the photography range of the PS-OCT apparatus 100 (also referred to as acquiring range or acquiring position) and a dotted photography region frame 442 indicating the photography range of the reference image that has already been positioned are displayed superimposed on the fundus image 411. An indicator 416 (i.e., color bar or numerical value) indicating the degree of match in position between the reference image and the image being shot now. It is sufficient for one of the photography region frame 442 on the reference image and the indicator 416 indicating the degree of match of positioning to be displayed, to continue automatic positioning before shooting.

The operator shoots a tomographic image by using an instruction device (not illustrated) such as a mouse or the like to specify the capture instruction button 414 displayed in the window 400 using the cursor, and clicking. For example, the operator specifies the capture instruction button 414 taking the degree of matching at the indicator 416 into consideration. While instructing shooting using automatic positioning has been described in the present embodiment, if the automatic positioning does not yield desired results, the operator can abort the automatic positioning and switch to shooting instructions by manual positioning.

The mouse in this embodiment includes, for example, a sensor to detect motion signals when the mouse is moved two-dimensionally by the hand of the user, two mouse buttons, left and right, to detect pressing by the hand of the user, and a wheel mechanism which is provided between the two left and right mouse buttons and which can be rotated forwards and backwards. The instruction device may be such that a display unit is provided with touch panel functions, so that acquisition positions are specified on the touch panel.

Measurement light is emitted from the light source 101 and light source 141, return light from the fundus Er is received at the line cameras 129 and 133 and APDs 152 and 153, and images are generated at the image generating unit 193 as described above.

Step S307: Image Analysis

An example of a method to detect the boundary of the layers of the retina is to use the luminance value obtained from the position calculated by DOPU in Expression (4) as a threshold value for layer detection. For example, a threshold value to be used to find the boundary of each layer in a healthy eye is input, or selected beforehand. The average luminance value of the RPE and overall retina layer region is also input beforehand or selected. The luminance value of the RPE at the position obtained by calculating Expression 4 and the overall retina layer region are compared with an average luminesce value input or selected beforehand. The threshold input or selected beforehand is adjusted depending on how many percent the difference in luminance value is. For example, in a case where the luminance value of the luminance image corresponding to the RPE 210 and retina layer region 220 in FIG. 2E is 10% lower than the average luminance value input of selected beforehand, the threshold is lowered by 10%. The image analyzing unit 194 then applies a median filter and a Sobel filter to the tomographic image to be processed, and creates images by each (hereafter also referred to as "median image" and "Sobel image"). Next, a profile is created for each A scan, from the created median image and Sobel image. A luminance value profile is created from the median image, and a gradient profile is created from the Sobel image. Peaks are detected in the profile created from the Sobel image. The profile of the median image corresponding to nearby the detected peaks or between the peaks is referenced, and compared with the threshold obtained earlier, whereby the regions of the retina layer or the boundaries thereof (e.g., the ILM, the ganglion cell layer (GCL), the inner plexiform layer (IPL), external limiting membrane (ELM), and photoreceptor inner segment/outer segment (IS/OS) junction) are extracted.

Step S308: Display

Next, the output processing of the generated images and analysis results will be described. Upon the generating and analysis of the images ending at the image generating unit 193 and image analyzing unit 194 within the signal processing unit 190, the display control unit 191 generates output information based on the results thereof, and outputs to the display unit 192 for display. The image analyzing unit 194 generates difference information based on the positioning results by the image overlaying unit 195.

Figure 6:
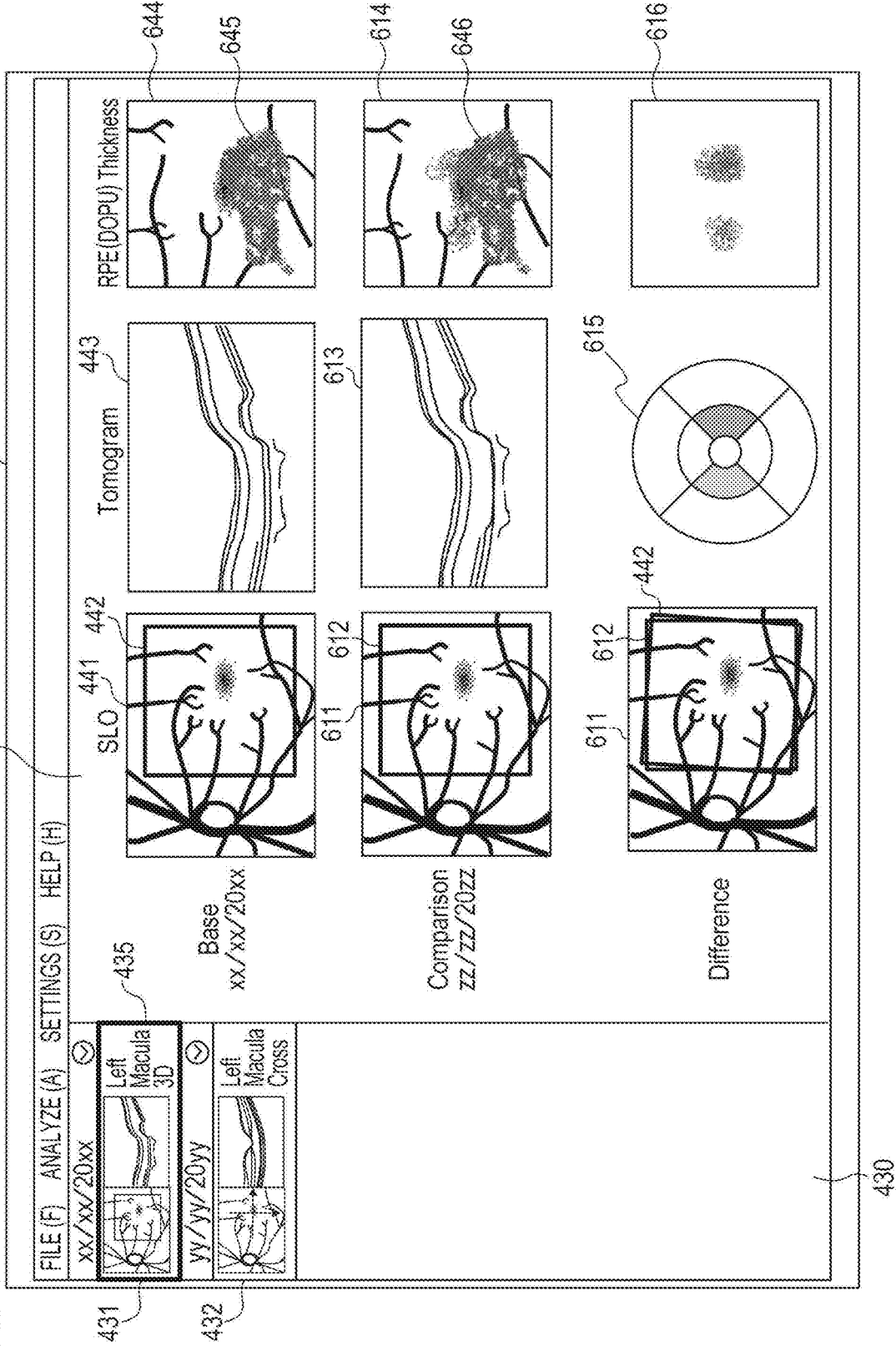
FIG. 6 is a display example of a display screen on the display unit of the image processing apparatus according to the first embodiment.

FIG. 6 is an example of a display on the display unit 192 according to the present embodiment, and more specifically is a display example of having performed follow up photography. The window 400 displayed on the display unit 192 has display regions 430 and 610. The display region 430 displays thumbnails 431 and 432 of photography data of the same object shot earlier, and a selection indicator 435 displayed on the thumbnail that has been selected as a reference. Displayed in the display region 610 are a fundus image 441, a tomographic image 443, and a thickness map 644 in which RPE thickness created from DOPU images has been superimposed on a fundus image within the range of the photography region frame 442, selected as a reference image (Base). In the thickness map 644, a region 645 schematically represents regions with abnormal thicknesses (pathological abnormality regions that are too thick, too thin, absent, etc.). A region where the retina layer thickness is abnormal is a region where the retina layer thickness falls outside of a normal range when compared with a normal retinal layer thickness database. In addition, a fundus image 611 and tomographic image 613 shot as comparison images, and a map 614 thereof are displayed. Further, difference results thereof, an Early Treatment Diabetic Retinopathy Study (ETDRS) difference grid 615, and a difference map 616 are displayed. Note that the ETDRS difference grid 615 displays the results of averaging difference values in each of multiple regions in the difference map 616. The grid shown here has concentric circles with diameters of 1 mm, 3 mm, and 6 mm, centered at a predetermined position, divided four ways.

Step S309: Determination of Whether or not to End

Determination is made in step S309 whether or not to end follow up photography. When transitioning to selection of whether to end the follow up photography or to transition to step S302 to select the photography mode, the positioning results by the image overlaying unit 195 and the analysis results by the image analyzing unit. 194 in the processing obtained in the processing so far are stored in the storage unit. Note that the image analyzing unit 194 stores not only the retina layer detection results but also information relating to regions with abnormal retina layer thicknesses (pathological abnormality regions that are too thick, too thin, absent, etc.), and difference results thereof, in the storage unit.

As described above, according to the present embodiment, positioning is performed at photography in follow up with polarization sensitive OCT images, using components in polarization fundus images unique to polarized light. Performing positioning using components unique to polarized light as in the present embodiment allows the same position as a previously-photograph position to be compared without being influenced by diseased areas. Positioning is performed up to immediately before instructing photography, so photography of approximately the same position can be performed.

Note that the position of the display region for displaying these images is not restricted to the arrangement described in the present invention, and fundus images may be displayed at the display region to the left side of the display screen, for example. Also, while an RPE thickness map has been illustrated as analysis results, the present embodiment is not restricted thusly, and this may be an overall thickness map of the retina layers, or may be an RNFL thickness map. In a case of glaucoma, a map of analyzed polarized light components such as a retardation map may be displayed.

Second Embodiment: Positioning After Photography

The first embodiment has been described above as an arrangement regarding follow up, where a polarization-sensitive tomographic image of the reference image selected at the time of photography, and a polarization-sensitive tomographic image created from images being aligned, are positioned, following which photography is performed. Conversely, in a second embodiment, the order of positioning and photography are reversed in follow up. That is to say, the polarization-sensitive tomographic image serving as a reference image and a polarization-sensitive tomographic image after photography are positioned.

Specifically, step S305 in FIG. 3 is replaced with a step S315 (not illustrated), and step S306 with a step S316 (not illustrated). Other steps are the same, so description thereof will be omitted.

Step S315: Photography

In step S315, a reference image for follow up is selected, following which various types of photography parameters of the apparatus are adjusted, and subsequently positioning is manually performed and photography is performed. A fundus image 411 imaged by the PS-SLO 140 and generated at the signal processing unit 190 (also referred to as luminance fundus image or two-dimensional fundus image) is displayed in the display region 410 (also referred to as first display region) in FIG. 4. A solid line frame 412 indicating the photography range of the PS-OCT apparatus 100 (also referred to as acquiring range or acquiring position) is displayed superimposed on the fundus image 411. In the present embodiment, description will be made regarding a case where manual is selected at the positioning selection button 415, instead of automatic processing.

The operator decides a photography position using an operating device (joystick or mouse) omitted from illustration, while watching the images 411, 421, 443, and so forth, displayed on the window 400. The operator then shoots a tomographic image by specifying the photography instruction button 414 displayed in the window 400 and clicking or the like.

Measurement light is emitted from the light source 101 and light source 141, return light from the fundus Er is received at the line cameras 129 and 133 and APDs 152 and 153, and images are generated at the image generating unit 193 as described above.

Step S316: Positioning

In step S316, positioning is performed in follow up to compare change in state of the retina layer at the same position as in the reference image selected in step S303. For example, the image overlaying unit 195 performs positioning using a polarization fundus image (e.g., retardation map) created when shooting the reference image selected in step S303, and the polarization fundus image created from the image shot in step S315. The method of positioning by the image overlaying unit 195 is the same as the method described in step S305, so description will be omitted.

As described above, according to the present embodiment, positioning is performed after photography in follow up with polarization sensitive OCT images, using components in polarization fundus images unique to polarized light. Performing positioning using components unique to polarized light at positions not readily affected by disease allows the same position as a previously-photograph position to be compared without being influenced by diseased areas. Positioning is performed using images after photography, so photography of approximately the same position can be performed even if not being away of positioning when shooting.

An arrangement may be made where the scanning positions of the galvano mirrors at the time of having obtained polarization-sensitive tomographic images in the past are stored in the storage unit, so that the scanning positions can be searched from the storage unit before photography, and the new polarization-sensitive tomographic image acquired based on the search scanning positions. In this case, the positioning in step S306 can be accurately performed even if there is positioning shift between past photography positions and the photography position this time, due to involuntary eye movement of the eye at the time of photography.

The scanning position is stored in the storage unit in a manner where coordinates (x, y) centered on the macula of the fundus (fixation position as to fixation target) is correlated with past image data. Alternatively, the scanning position may be stored in the storage unit with the scanning angle of the galvano mirror correlated with the past image data.

Also, the positioning results may be reflected in past and current polarization-sensitive tomographic images after having performed positioning. Specifically, display is made in a format where the acquisition position of the current polarization-sensitive tomographic image is shown in a past polarization-sensitive tomographic image, and in a format where the acquisition position of a past polarization-sensitive tomographic image is shown in the current polarization-sensitive tomographic image. The display format showing the acquisition position is, for example, the outer frame of the acquisition position.

Further, an image may be generated and displayed on the display unit 192, which shows the difference between the positioned past and current polarization-sensitive tomographic images.

Also, the results of positioning the past and current polarization-sensitive tomographic images may be reflected in the past and current tomographic luminance images corresponding to the past and current polarization-sensitive tomographic images. The results of positioning of the past and current polarization-sensitive tomographic images may be displayed on the display unit 192 alongside the past and current polarization-sensitive tomographic images used for the reflecting thereof.

Third Embodiment: Positioning Before Photography and After Photography

The second embodiment has been described above as an arrangement regarding follow up, where the polarization planar image serving as a reference image and a polarization planar image after photography are positioned. Conversely, in a third embodiment, a polarization planar image of a reference image, and a polarization planar images of both before photography and after photography, are used positioning.

Specifically, step S305 in FIG. 3 is replaced with a step S325-1 (not illustrated), and step S306 with a step S326 (not illustrated). Further, a step S325-2 (not illustrated) is added after step S326. Other steps are the same as with the first embodiment, so description thereof will be omitted.

Step S325-1: Positioning Before Photography

In step S325-1, positioning is performed to shoot the same position as the reference image selected in step S303, for follow up. Description will be made in the present embodiment regarding a case where Auto has been selected by the positioning selection button 415 in FIG. 4. The image overlaying unit 195 performs positioning using a polarization fundus image (e.g., retardation map) created when shooting the reference image selected in step S303, and a polarization fundus image created by the eye while performing alignment. The method of positioning by the image overlaying unit 195 is the same as the method described in step S305, so description will be omitted.

Step S326: Photography

In step S326, the operator selects a reference image for follow up, and performs photography after having viewed the results of automatic positioning by the image overlaying unit 195. The operator shoots a tomographic image by using an instruction device (not illustrated) such as a mouse or the like to specify the capture instruction button 414 displayed in the window 400 using the cursor, and clicking. For example, the operator specifies the capture instruction button 414 taking the degree of matching of positioning between the reference image and image being shot at the indicator 416 into consideration.

Step S325-2: Positioning Also after Photography

In step S325-2, positioning is performed in follow up to compare change in state of the retina layer at the same position as in the reference image selected in step S303. Since photography has been performed involving positioning in step S325-1, the processing here is correction of positional shift at the timing at which the photography instruction was actually given. The image overlaying unit 195 performs positioning using the polarization fundus image (e.g., retardation map) created when shooting the reference image selected in step S303, and the polarization fundus image created from the image shot in step S326. The method of positioning by the image overlaying unit 195 is the same as the method described in step S305, so description will be omitted.

As described above, according to the present embodiment, positioning is performed before and after photography in follow up with polarization sensitive OCT images, using components in polarization fundus images unique to polarized light. Performing positioning using components unique to polarized light at positions not readily affected by disease allows the same position as a previously-photograph position to be compared without being influenced by diseased areas. Positioning is performed up to immediately before instructing photography, and positioning is also performed after photography to correct positional shift at the time of instructing photography. Accordingly, change over time can be compared at approximately the same position as the last time.

Fourth Embodiment: Superimposed Display of Information Relating to Pathological Abnormality on Image after Positioning The first through third embodiments have been described above as arrangements regarding follow up, where a Polarization planar image of a reference image, and at least one of a polarization planar image before Photography and a polarization planar image after photography, are positioned. Conversely, in a fourth embodiment, information relating to a pathological abnormality is displayed superimposed on the image following positioning. This facilitates follow up of change of the disease. The present embodiment will be described with reference to FIG. 7. FIG. 7 is a display example of a display screen on the display unit of the image processing apparatus according to a fourth embodiment.

The dashed line 1001 and dotted line 1002 represent outlines of pathological abnormality regions. The dashed line 1001 represents the outline of a pathological abnormality region 645 detected from a PS-OCT tomographic image 443 of a reference image, which is read out from the storage unit and displayed. The dotted line 1002 represents the outline of a pathological abnormality region 646 detected from a PS-OCT tomographic image 613 of the photographed image, which has been detected from the analysis results from the image analyzing unit 194. These pathological abnormality regions represent regions with abnormal RPE thickness created from DOPU images (pathological abnormality regions that are too thick, too thin, absent, etc.). While representation has been made in the present embodiment with dashed liens and dotted lines, the display format is not restricted to this, and any format may be used as long as identifiable, such as using different colors, degrees of transparency, types of lines, and so forth. Also, while the pathological abnormality regions of both the reference image and photographed image are displayed superimposed in the example, but the present embodiment is not restricted to this, and difference regions may be displayed, for example. In a case of displaying difference regions, display is preferably made such that whether the pathological abnormality region has spread or regressed can be understood. For example, this may be differentiated by color, such as displaying in red if spread, and displaying in blue if regressed. Alternatively marks representing spread or regress may be displayed.

According to the present embodiment as described above, follow up using polarization OCT images is facilitated by displaying difference between past pathological abnormality regions and current pathological abnormality regions in an easily understandable manner.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-159178, filed Jul. 31, 2013, which is hereby incorporated by reference herein in its entirety.

The invention claimed is:

1. A photography apparatus for acquiring a plurality of polarization-sensitive tomographic images of an object using information about light having polarization different from each other, combined light being obtained by combining return light from the object irradiated by measurement light and reference light corresponding to the measurement light, the combined light being split into the light having polarization different from each other, the photography apparatus comprising:
    a selecting unit configured to select one of a plurality of photography modes, including a follow up photography mode;
    a tomographic image acquiring unit configured to acquire the plurality of polarization-sensitive tomographic images obtained by photographing the object at different times; and
    a positioning unit configured to, in a case where the follow up photography mode is selected, position the plurality of polarization-sensitive tomographic images using information about a plurality of polarization planar images of the object corresponding to the plurality of polarization-sensitive tomographic images.

2. The photography apparatus according to claim 1, wherein the object is an eye,
    wherein the plurality of polarization planar images is a plurality of retardation maps of a fundus of the eye,
    and wherein, in a case where there is a deformity over time in a retinal pigment epithelium (RPE) layer of the fundus in the plurality of polarization-sensitive tomographic images, the positioning unit positions the plurality of polarization-sensitive tomographic images using information about the plurality of retardation maps of a nerve fiber layer (NFL) of the fundus.

3. The photography apparatus according to claim 1,
    wherein the object is an eye,
    wherein the plurality of polarization planar images is a plurality of DOPU maps of a fundus of the eye, and wherein, in a case where there is a deformity over time in a retinal nerve fiber layer (RNFL) of the fundus in the plurality of polarization-sensitive tomographic images, the positioning unit positions the plurality of polarization-sensitive tomographic images using information about the plurality of DOPU maps of the RPE layer of the fundus.

4. The photography apparatus according to claim 1, wherein, after the positioning unit performs the positioning, the tomographic image acquiring unit acquires a new polarization-sensitive tomographic image of the object, and wherein the positioning unit positions, using information about a plurality of polarization planar images of the object corresponding to the new polarization-sensitive tomographic image and a past polarization-sensitive tomographic image, the new polarization-sensitive tomographic image and the past polarization-sensitive tomographic image.

5. The photography apparatus according to claim 1, further comprising:
a display control unit configured to display a plurality of polarization planar images corresponding to the plurality of polarization-sensitive tomographic images that have been positioned on a display unit, and to display a display form representing a pathological abnormality region in the object, superimposed on the plurality of polarization planar images.

6. The photography apparatus according to claim 1, further comprising:
an image generating unit configured to generate an image indicating difference among the plurality of polarization-sensitive tomographic images.

7. The photography apparatus according to claim 1 further comprising:
an image generating unit configured to generate the plurality of polarization planar images using information about the plurality of polarization-sensitive tomographic images.

8. The photography apparatus according to claim 1, wherein the object is an eye,
wherein the plurality of polarization planar images is a plurality of retardation maps of a fundus of the eye or a plurality of DOPU maps of the fundus of the eye,
and wherein the positioning unit positions the plurality of polarization-sensitive tomographic images using information about the plurality of retardation maps of a retinal nerve fiber layer of the fundus or using information about the plurality of DOPU maps of a retinal pigment epithelium layer of the fundus.

9. A photography method for acquiring a plurality of polarization-sensitive tomographic images of an object using information about light having polarization different from each other, combined light being obtained by combining return light from the object irradiated by measurement light and reference light corresponding to the measurement light, the combined light being split into the light having polarization different from each other, the photographic method comprising:
a step to select one of a plurality of photography modes, including a follow up photography mode;
a step to acquire the plurality of polarization-sensitive tomographic images obtained by photographing the object at different times; and
a step to, in a case where the follow up photography mode is selected, position the plurality of polarization-sensitive tomographic images using information about a plurality of polarization planar images of the object corresponding to the plurality of polarization-sensitive tomographic images.

10. The photography method according to claim 9, wherein the object is an eye,
wherein the plurality of polarization planar images is a plurality of retardation maps of a fundus of the eye or a plurality of DOPU maps of the fundus of the eye,
and wherein the plurality of polarization-sensitive tomographic images is positioned using information about the plurality of retardation maps of a retinal nerve fiber layer of the fundus or using information about the plurality of DOPU maps of a retinal pigment epithelium layer of the fundus.

11. The photography method according to claim 9, wherein, in the step to acquire the plurality of polarization-sensitive tomographic images, after the positioning step is performed a new polarization-sensitive tomographic image of the object is performed, and
wherein, using information about a plurality of polarization planar images of the object corresponding to the new polarization-sensitive tomographic image and a past polarization-sensitive tomographic image, the new polarization-sensitive tomographic image and the past polarization-sensitive tomographic images are positioned.

12. The photography method according to claim 9, further comprising:
a step to display a plurality of polarization planar images corresponding to the plurality of polarization-sensitive tomographic images that have been positioned on a display unit, and to display a display form representing a pathological abnormality region in the object, superimposed on the plurality of polarization planar images.

13. A non-transitory computer-readable storage medium storing a program for causing a computer to execute the steps of the photography method according to claim 9.

14. An image processing apparatus comprising:
a tomographic image acquiring unit configured to acquire a plurality of polarization-sensitive tomographic images obtained by photographing an object at different times; and
a positioning unit configured to position the plurality of polarization-sensitive tomographic images using information about a plurality of polarization planar images of the object corresponding to the plurality of polarization-sensitive tomographic images, the plurality of polarization planar images being a plurality of retardation maps of the object or a plurality of DOPU maps of the object.

15. The image processing apparatus according to claim 14, wherein:
the object is an eye;
the plurality of polarization planar images is a plurality of retardation maps of a fundus of the eye or a plurality of DOPU maps of the fundus of the eye; and
the positioning unit positions the plurality of polarization-sensitive tomographic images using information about the plurality of retardation maps of a retinal nerve fiber layer of the fundus or using information about the plurality of DOPU maps of a retinal pigment epithelium layer of the fundus.

16. An image processing method comprising:
a step to acquire a plurality of polarization-sensitive tomographic images obtained by photographing an object at different times; and a step to position the plurality of polarization-sensitive tomographic images using information about a plurality of polarization planar images of the object corresponding to the plurality of polarization-sensitive tomographic images, the plurality of polarization planar images being a plurality of retardation maps of the object or a plurality of DOPU maps of the object.

17. A non-transitory computer-readable storage medium storing a program for causing a computer to execute the steps of the image processing method according to claim 16.

18. The image processing method according to claim 16, wherein:
the object is an eye;
the plurality of planar images is a plurality of retardation maps of a fundus of the eye or a plurality of DOPU maps of the fundus of the eye; and
the plurality of polarization-sensitive tomographic images is positioned using information about the plurality of retardation maps of a retinal nerve fiber layer of the fundus or using information about the plurality of DOPU maps of a retinal pigment epithelium layer of the fundus.

* * * * *